(12) United States Patent
Campbell et al.

(10) Patent No.: US 8,346,327 B2
(45) Date of Patent: Jan. 1, 2013

(54) METHOD FOR IDENTIFICATION OF SENSOR SITE BY LOCAL SKIN SPECTRUM DATA

(75) Inventors: Shannon E. Campbell, Oakland, CA (US); Martin P. Debreczeny, Danville, CA (US); Carine Hoarau, Lafayette, CA (US)

(73) Assignee: Covidien LP, Mansfield, MA (US)

( * ) Notice: Subject to any disclaimer, the term of this patent is extended or adjusted under 35 U.S.C. 154(b) by 1472 days.

(21) Appl. No.: 11/716,264

(22) Filed: Mar. 9, 2007

(65) Prior Publication Data

US 2008/0221410 A1  Sep. 11, 2008

(51) Int. Cl.
*A61B 5/1455* (2006.01)

(52) U.S. Cl. .................................... 600/310; 600/323

(58) Field of Classification Search ............... 600/310, 600/323, 331, 322, 324, 326, 316, 473–478
See application file for complete search history.

(56) References Cited

U.S. PATENT DOCUMENTS

| | | |
|---|---|---|
| 3,998,550 A | 12/1976 | Konishi et al. |
| 4,066,068 A | 1/1978 | Nilsson et al. |
| 4,364,008 A | 12/1982 | Jacques |
| 4,621,643 A * | 11/1986 | New et al. ............. 600/331 |
| 4,711,244 A | 12/1987 | Kuzara |
| 4,723,554 A | 2/1988 | Oman et al. |
| 4,805,365 A | 2/1989 | Bastian |
| 4,850,365 A | 7/1989 | Rosenthal |
| 4,860,753 A | 8/1989 | Amerena |
| 4,883,055 A | 11/1989 | Merrick |
| 4,907,594 A | 3/1990 | Muz |
| 5,057,695 A | 10/1991 | Hirao et al. |
| 5,058,588 A | 10/1991 | Kaestle |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |
| 5,277,181 A | 1/1994 | Mendelson et al. |
| 5,279,295 A | 1/1994 | Martens et al. |
| 5,282,467 A | 2/1994 | Piantadosi et al. |
| 5,285,783 A | 2/1994 | Secker |
| 5,337,745 A | 8/1994 | Benaron |
| 5,337,937 A | 8/1994 | Remiszewski et al. |
| 5,348,004 A | 9/1994 | Hollub |
| 5,355,880 A | 10/1994 | Thomas et al. |
| 5,372,136 A * | 12/1994 | Steuer et al. ............. 600/326 |

(Continued)

FOREIGN PATENT DOCUMENTS

CA  2353007 A1  6/2000

(Continued)

OTHER PUBLICATIONS

U.S. Appl. No. 11/528,154, filed Sep. 27, 2006, Debreczeny et al.

(Continued)

*Primary Examiner* — Eric Winakur
*Assistant Examiner* — Chu Chuan (JJ) Liu

(57) ABSTRACT

A method is provided for determining the location of the sensor. The method comprises determining a physiological parameter based on detected light and determining the location of the sensor based on the physiological parameter. In addition, a method is provided for operating a sensor that includes calibrating a sensor based on a patient-specific physiological parameter, in which the patient-specific physiological parameter is skin color, age, gender, pooled blood, venous blood pulsation, or abnormal tissue.

22 Claims, 3 Drawing Sheets

U.S. PATENT DOCUMENTS

| | | | |
|---|---|---|---|
| 5,377,674 A | | 1/1995 | Kuestner |
| 5,499,627 A | | 3/1996 | Steuer et al. |
| 5,529,065 A | * | 6/1996 | Tsuchiya ............... 600/310 |
| 5,615,689 A | | 4/1997 | Kotler |
| 5,687,721 A | | 11/1997 | Kuhls |
| 5,701,902 A | | 12/1997 | Vari et al. |
| 5,720,284 A | | 2/1998 | Aoyagi et al. |
| 5,725,480 A | * | 3/1998 | Oosta et al. ............... 600/310 |
| 5,735,284 A | | 4/1998 | Tsoglin et al. |
| 5,747,789 A | | 5/1998 | Godik |
| 5,755,672 A | | 5/1998 | Arai et al. |
| 5,788,643 A | | 8/1998 | Feldman |
| 5,803,908 A | | 9/1998 | Steuer et al. |
| 5,827,181 A | | 10/1998 | Dias et al. |
| 5,833,602 A | | 11/1998 | Osemwota |
| 5,853,364 A | | 12/1998 | Baker, Jr. et al. |
| 5,860,919 A | | 1/1999 | Kiani-Azarbayjany et al. |
| 5,906,582 A | | 5/1999 | Kondo et al. |
| 6,064,898 A | | 5/2000 | Aldrich |
| 6,125,297 A | | 9/2000 | Siconolfi |
| 6,149,591 A | | 11/2000 | Henderson et al. |
| 6,178,342 B1 | | 1/2001 | Borgos et al. |
| 6,222,189 B1 | | 4/2001 | Misner et al. |
| 6,246,894 B1 | | 6/2001 | Steuer et al. |
| 6,280,396 B1 | | 8/2001 | Clark |
| 6,336,044 B1 | | 1/2002 | Ghiassi et al. |
| 6,370,426 B1 | | 4/2002 | Campbell et al. |
| 6,400,971 B1 | | 6/2002 | Finarov et al. |
| 6,402,690 B1 | | 6/2002 | Rhee et al. |
| 6,442,408 B1 | | 8/2002 | Wenzel et al. |
| 6,456,870 B1 | * | 9/2002 | Rennert et al. ............ 600/310 |
| 6,466,807 B1 | | 10/2002 | Dobson et al. |
| 6,488,677 B1 | | 12/2002 | Bowman et al. |
| 6,493,566 B1 | * | 12/2002 | Kees et al. ............... 600/310 |
| 6,512,936 B1 | | 1/2003 | Monfre et al. |
| 6,591,122 B2 | | 7/2003 | Schmitt |
| 6,591,123 B2 | * | 7/2003 | Fein et al. ............... 600/323 |
| 6,592,574 B1 | | 7/2003 | Shimmick et al. |
| 6,600,946 B1 | | 7/2003 | Rice |
| 6,606,509 B2 | | 8/2003 | Schmitt |
| 6,615,064 B1 | | 9/2003 | Aldrich |
| 6,635,491 B1 | | 10/2003 | Khalil et al. |
| 6,636,759 B2 | | 10/2003 | Robinson |
| 6,643,543 B2 | | 11/2003 | Takehara et al. |
| 6,654,620 B2 | | 11/2003 | Wu et al. |
| 6,668,181 B2 | | 12/2003 | Wenzel et al. |
| 6,675,029 B2 | | 1/2004 | Monfre et al. |
| 6,687,519 B2 | | 2/2004 | Steuer et al. |
| 6,777,240 B2 | | 8/2004 | Hazen et al. |
| 6,849,046 B1 | | 2/2005 | Eyal-Bickels et al. |
| 6,873,865 B2 | | 3/2005 | Steuer et al. |
| 6,882,874 B2 | | 4/2005 | Huiku |
| 6,950,699 B1 | | 9/2005 | Manwaring et al. |
| 7,027,849 B2 | | 4/2006 | Al-Ali |
| 7,142,901 B2 | | 11/2006 | Kiani et al. |
| 7,236,811 B2 | | 6/2007 | Schmitt |
| 7,239,902 B2 | | 7/2007 | Schmitt et al. |
| 7,277,741 B2 | | 10/2007 | Debreczeny et al. |
| 7,343,186 B2 | | 3/2008 | Lamego et al. |
| 7,430,444 B2 | | 9/2008 | Pologe et al. |
| 7,657,292 B2 | | 2/2010 | Baker et al. |
| 8,135,448 B2 | | 3/2012 | Baker et al. |
| 2001/0020122 A1 | | 9/2001 | Steuer et al. |
| 2003/0060693 A1 | | 3/2003 | Monfre et al. |
| 2004/0127777 A1 | | 7/2004 | Ruchti et al. |
| 2004/0147034 A1 | | 7/2004 | Gore et al. |
| 2004/0230106 A1 | | 11/2004 | Schmitt et al. |
| 2005/0070773 A1 | | 3/2005 | Chin et al. |
| 2005/0131286 A1 | | 6/2005 | Parker et al. |
| 2005/0168722 A1 | | 8/2005 | Forstner et al. |
| 2005/0192488 A1 | | 9/2005 | Bryenton et al. |
| 2005/0192493 A1 | | 9/2005 | Wuori |
| 2005/0250998 A1 | | 11/2005 | Huiku |
| 2005/0267346 A1 | | 12/2005 | Faber et al. |
| 2006/0020181 A1 | | 1/2006 | Schmitt |
| 2006/0052680 A1 | | 3/2006 | Diab |
| 2006/0084864 A1 | | 4/2006 | Schmitt et al. |
| 2006/0122475 A1 | | 6/2006 | Balberg et al. |
| 2006/0129037 A1 | | 6/2006 | Kaufman et al. |
| 2006/0129038 A1 | | 6/2006 | Zelenchuk et al. |
| 2006/0167350 A1 | | 7/2006 | Monfre et al. |
| 2006/0247506 A1 | | 11/2006 | Balberg et al. |
| 2006/0253016 A1 | | 11/2006 | R. Baker et al. |
| 2006/0276696 A1 | | 12/2006 | Schurman et al. |
| 2007/0043269 A1 | | 2/2007 | Mannheimer et al. |
| 2007/0073127 A1 | | 3/2007 | Kiani et al. |
| 2007/0106137 A1 | | 5/2007 | Baker et al. |
| 2007/0118027 A1 | | 5/2007 | Baker et al. |
| 2007/0129614 A1 | | 6/2007 | Schmitt et al. |
| 2007/0244376 A1 | | 10/2007 | Wang |
| 2007/0282178 A1 | | 12/2007 | Scholler et al. |
| 2007/0282183 A1 | | 12/2007 | Scholler et al. |
| 2008/0004513 A1 | | 1/2008 | Walker et al. |
| 2008/0081969 A1 | | 4/2008 | Feldman et al. |
| 2008/0154104 A1 | | 6/2008 | Lamego et al. |
| 2008/0221409 A1 | | 9/2008 | Hoarau |

FOREIGN PATENT DOCUMENTS

| | | |
|---|---|---|
| DE | 19855521 A1 | 6/2000 |
| EP | 1135184 A1 | 6/2000 |
| EP | 1184663 A2 | 3/2002 |
| EP | 1491135 | 12/2004 |
| FR | 2710517 | 4/1995 |
| JP | 4-40940 | 2/1992 |
| JP | 5-329163 | 12/1993 |
| JP | 11-244266 | 9/1999 |
| JP | 2004 081427 A | 3/2004 |
| JP | 25278758 | 10/2005 |
| JP | 26075354 | 3/2006 |
| WO | WO 95/19562 A | 7/1995 |
| WO | WO 98/34097 | 8/1998 |
| WO | WO 00/32262 A1 | 6/2000 |
| WO | WO 00/71025 A | 11/2000 |
| WO | WO 93/13706 A2 | 1/2001 |
| WO | WO 01/16577 A1 | 3/2001 |
| WO | 0163251 A | 8/2001 |
| WO | WO 03/010510 A | 2/2003 |
| WO | 20050041765 A | 5/2005 |
| WO | WO 2005/041765 A | 5/2005 |
| WO | 2006124455 | 11/2006 |
| WO | 20070017263 A | 2/2007 |

OTHER PUBLICATIONS

U.S. Appl. No. 11/528,218, filed Sep. 27, 2006, Campbell, et al.
U.S. Appl. No. 11/529,024, filed Sep. 28, 2006, Agashe, et al.
U.S. Appl. No. 11/541,010, filed Sep. 29, 2006, Baker, Jr., et al.
Wheeler, Owen H., "Near Infrared Spectra of Organic Compounds," Department of Chemistry, College of Agriculture and Mechanic Arts, University of Puerto Rico (Mar. 1929).
Pace, Nello, et al., "Studies on Body Composition: III. The body water and chemically combined nitrogen content in relation to fat content," Naval Medical Research Institute, Bethesda, Maryland (Jan. 11, 1945).
Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).
Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).
Forbes, R.M., et al., "The Composition of the Adult Human Body as Determined by Chemical Analysis," Division of Animal Nutrition, and the Department of Anatomy, University of Illinois, Jan. 19, 1953.
Buijs, K., et al., "Near-Infrared Studies of the Structure of Water. I. Pure Water," *The Journal of Chemical Physics*, vol. 39, No. 8, pp. 2035-2041 (Oct. 15, 1963).
Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).
Goldstein, R., et al., "The Near-Infrared Absorption of Liquid Water at Temperatures Between 27 and 209° C," *J. Quant. Spectrosc. Radiat Transfer*., vol. 4, pp. 441-451 (1964).

Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).
Houseman, R.A., et al., "The measurement of total body water in living pigs by deuterium oxide dilution and its relation to body composition," *Br. J. Nutr.*, vol. 30, pp. 149-156 (1973).
Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).
Lesser, G.T., et al., "Body water compartments with human aging using fat-free mass as the reference standard," *Am J. Physiol Regul Integr Comp Physiol.*, vol. 236, pp. 215-220 (1979).
Sheng, Hwai-Ping, et al., "A review of body composition studies with emphasis on total body water and fat," *The American Journal of Clinical Nutrition*, vol. 32., pp. 630-647 (Mar. 1979).
Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp.146-149 (1980).
Fomon, Samuel J., et al., "Body composition of reference children from birth to age 10 years," The American Journal of clinical Nutrition, vol. 35, pp. 1169-1175, (May 1982).
Lanza, Elaine, "Determination of Moisture, Protein, Fat, and Calories in Raw Pork and Beef by near Infrared Spectroscopy," *Journal of Food Science*, vol. 48, pp. 471-474 (1983).
Shields, R. G., Jr., et al., "Efficacy of Deuterium Oxide to Estimate Body Composition of Growing Swine"; *Journal of Animal Science*, vol. 57, No. 1, pp. 66-73, (1983).
Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).
Cohn, S.H., et al., "Assessment of cellular mass and lean body mass by noninvasive nuclear techniques," *J. Lab Clin Med.*, vol. 105, pp. 305-311 (1985).
Hannon, John P., et al., "Splenic red cell sequestration and blood volume measurements in conscious pigs," *Am J. Physiol.*, vol. 248, pp. R293-R301 (1985).
Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).
Cox, Patrick, et al., "Variations in Lipids in Different Layers of Porcine Epidermis," *J. Invest Dermatol.*, vol. 87, pp. 741-744 (1986).
Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).
Hedberg, Chrisopher L., et al., "The Time Course of Lipid Biosynthesis in Pig Epidermis," *J. Invest Dermatol.*, vol. 91, pp. 169-174 (1988).
Hedberg, Christopher L., et al., "The nonpolar Lipids of Pig Epidermis," *J. Invest Dermatol.*, vol. 90, pp. 225-229 (1988).
Trapp, Scott A., et al., "An improved spectrophotometric bromide assay for the estimation of extracellular water volume," *Clinica Chimica Acta.*, vol. 181, pp. 207-212, (1989).
Bommannan, D., et al., "Examination of Stratum Corneum Barrier Function In Vivo by Infrared Spectroscopy," *J. Invest Dermatol*, vol. 95, pp. 403-408 (1990).
Hannon, John P., et al., "Normal pHysiological Values for Conscious Pigs Used in Biomedical Research," *Laboratory Animal Science*, vol. 40, No. 3, May 1990.
Mak, Vivien H.W., et al., "Oleic Acid Concentration and Effect in Human Stratum Corneum: Non-Invasive determination by Attenuated Total Reflectance Infrared Spectroscopy In Vivo," *Journal of Controlled Release*, vol. 12, pp. 67-75 (1990).
Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.
Drummer, C., et al., "Effects of an acute saline infusion on fluid and electrolyte metabolism in humans," *Am J. Physiol.*, vol. 262, pp. F744-F754 (1992).
Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).
Schmitt et al., *Proc. SPIE*, "Measurement of blood hematocrit by dual-wavelength near-IP photoplethysmography," 1641:150-161 (1992).
Diaz-Carrillo, E., et al., "Near infrared calibrations for goat's milk components; protein, total casein, as $\alpha_s$-, $\beta$- and $\gamma$-caseins, fat and lactose," *J. near Infrared Spectrosc.*, vol. 1, pp. 141-146 (1993).
Martin, K., "Direct Measurement of Moisture in Skin by NIR spectroscopy," *J. Soc. Cosmet Chem.*, 44:249-261 (1993).
Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).
Thompson et al., "Can bioelectrical impedance be used to measure total body water in dialysis patients?", *Physiol. Meas.*, 14:455-461 (1993).
Bewig, Karen M., et al., "Discriminant Analysis of Vegetable Oils by Near-Infrared Reflectance Spectroscopy," *JAOCS*, vol. 71, No. 2, pp. 195-200 (Feb. 1994).
Kamishikiryo-Yamashita, Hiromi, et al, "Protein Content in Milk by Near-Infrared Spectroscopy," *Journal of Food Science*, vol. 59, No. 2, pp. 313-315 (1994).
Matcher, S. J., et al., "Absolute quantification of deoxyhaemoglobin concentration in tissue near infrared spectroscopy," *Phys. Med. Biol.*, vol. 39, pp. 1295-1312 (1994).
Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).
Steven, Alasdair C., et al., "Protein composition of cornified cell envelopes of epidermal keratinocytes," *Journal of Cell Science*, vol. 107, pp. 693-700 (1994).
Takeo, T. et al., "Skin Hydration State Estimation Using a Fiber-Optic Refractometer," *Applied Optics*, vol. 33, No. 19, Jul. 1994, p. 4267-4272.
Warren, Joan L., et al., "The burden and Outcomes Associates with Dehydration among US Elderly, 1991," *American Journal of Public Health*, vol. 84, No. 8, pp. 1265-1269 (Aug. 1994).
Åneman, Anders, et al., "Splanchnic and Renal Sympathetic Activity in Relation to Hemodynamics During Isoflurane Administration in Pigs," *Anesth Analg.*, vol. 80, pp. 135-142, (1995).
Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).
Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).
Quiniou, N., et al., "Prediction of Tissular Body Composition from Protein and Lipid Deposition in Growing Pigs," *J. Anim. Sci.*, vol. 73, pp. 1567-1575, (1995).
Avis, N. J., et al.; "In vitro multifrequency electrical impedance measurements and modeling of the cervix in late pregnancy", *Physiological Measurement*, vol. 17, pp. A97-103, 1996.
Gniadecka, M., et al., "Assessment of dermal water by high-frequency ultrasound: comparative studies with nuclear magnetic resonance," *British Journal of Dermatology*, vol. 135, pp. 218-224, (1996).
Finn, Patrick J., et al., "Progressive celluarl dehydration and proteolysis in critically ill patients," The Lancet, vol. 347, pp. 654-646 (Mar. 9, 1996).
Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging *versus* Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. AppL Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water, " *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "Perspectives—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M380 (2001).

Divert, Victor E., "Body Thermal State Influence on Local Skin Thermosensitivity," *International Journal of Circumpolar Health*, vol. 60, pp. 305-311 (2001).

Du, Y., et al., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch—Eur J. Physiol*, vol. 442, pp. 362-368 (2001).

Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Kamba, Masayuki, et al., "Proton magnetic resonance spectroscopy for assessment of human body composition," *Am J. Clin. Nutr.*, vol. 73, pp. 172-176 (2001).

Lever, M., et al., "Some ways of looking at compensatory kosmotropes and different water environments," *Comparative Biochemistry and Physiolog.*, vol. 130, Part A, pp. 471-486, (2001).

Mingrone, G., et al., "Unreliable use of standard muscle hydration value in obesity," *Am J. Physiol Endocrinal Metab.*, vol. 280, pp. E365-371, (2001).

Ritz, Patrick, "Chronic Cellular Dehydration in the Aged Patient," *Journal of Gerontology*, vol. 56A, No. 6, pp. M349-M352 (2001).

Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P., et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Tsukahara, K., et al., "Dermal Fluid translocatiton is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogeneous group of adult humans," *Eur J. Appl. Physiol.*, vol. 85, pp. 326-332 (2001).

Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).

Watson, Walter, "Hydration of fat-free body mass: new physiological modeling approach," *Am J. Physiol. Endocrinol. Metab.*, Letters to the Editor, vol. 278, pp. E752-E753 (2001).

Attas, E. Michael, et al., "Near-IR Spectroscopic Imaging for Skin Hydration: the Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Blank, T.B., et al., "Clinical Results from a Non-Invasive Blood Glucose Monitor," *Photonics West 2002 Meeting*, San Jose, California, Jan. 19-25, 2002 (25 pages).

Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma Volume Expanders," *Anesthesiology*, vol. 96, No. 6, pp. 1371-1380 (Jun. 2002).

Endo, Yutaka, et al., "Changes in Blood Pressure and Muscle Sympathetic Nerve Activity during Water Drinking in Humans," *Japanese Journal of Physiology*, vol. 52, pp. 421-427 (2002).

Haga, Henning A., et al., "Motor responses to stimulation during isoflurane anaesthesia in pigs," *Veterinary Anaesthesia and Analgesia*, vol. 29, pp. 69-75 (2002).

Klaus, Stephan, et al., "Assessment of fluid balance by measurement of skin tissue thickness during clinical anaesthesia," *Clin. Physiol. & Func. Im.*, vol. 22, pp. 197-201 (2002).

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria, et al., "Charactrization of Reconstructed Skin Models," Skin Pharmacol Appl Skin Physiol., vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am J. Clin Nutr*., vol. 76, pp. 384-389 (2002).

Baković, Darija, et al., "Spleen volume and blood flow response to repeated breath-hold apneas," *J. Appl. Physiol.*, vol. 95, pp. 1460-1466 (2003).

Bartok, Cynthia, et al., "Measurement of nutritional status in simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum COrneum at Different Hydration Levels," *J. Invest Dermatol*, vol. 150, pp. 750-758 (2003).

Butte, Nancy F., et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of Trauma, Injury, Infection, and Critical Care*, vol. 54, No. 5, pp. S20-S25 (May Supplement 2003).

Cook, Lynda S., "IV Vluid Resuscitation," *Journal of Infusion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: issues for the 21$^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol. Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol., 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Mentes, Janet C., et al., "Reducing Hydration=-Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

PetäjäL., et al., "Dielectric constant of skin and subcutaneous fat to assess fluid changes after cardiac surgery", *Physiological Measurement*, 24: 3383-390, 2003.

Rhodes, Andrew, et al., "Book Report—Haemodynamic monitoring in critically ill patients," *Critical Care*, vol. 8, p. 203 (2004).

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Robinson, Martin P., et al., "A novel method of studying total body water content using a resonant cavity: experiments and numerical simulation," Phys. Med. Biol., vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab*, vol. 284, pp. E267-E273 (2003).

Windberger, U., et al., "Whole blood viscosity, plasma viscosity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *Physiol. Meas.*, vol. 25, pp. 447-454, (2004).

St-Onge, Marie-Pierre, et al., "Dual-energy X-ray absorptiometry lean soft tissue hydration: independent contributions of intra-and extracellular water," *Am J. Physiol. Endrocrinol Metab*, vol. 287, pp. E842-E847, Jul. 6, 2004.

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.oro/organizations/pubs/newsletters/leos/apr98/infrared.htm (last accessed, Nov. 30, 2005).

Haroun, D., et al., "Composition of the fat-free mass in obese and nonobese children: matched case—control analyses," *International Journal of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mit.edu/ProgressReports/HomeAutomation/Report2-5/Chapter04.pdf (last.accessed, Nov. 30, 2005).

García-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

ISR/PCT/US2008/003172; Date of mailing: Jun. 30, 2008.

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

Bickler, Philip E. et al.; Effects of Skin Pigmentation on Pulse Oximeter Accuracy at Low Saturation; Clinical Investigations; Apr. 2005; pp. 715-719; vol. 102, No. 4.

Egawa, Mariko et al.; Regional Difference of Water Content in Human Skin Studied by Diffuse-Reflectance Near-Infrared Spectroscopy: Consideration of Measurement Depth; Society for Applied Spectroscopy; 2006; pp. 24-28; vol. 60 No. 1.

\* cited by examiner

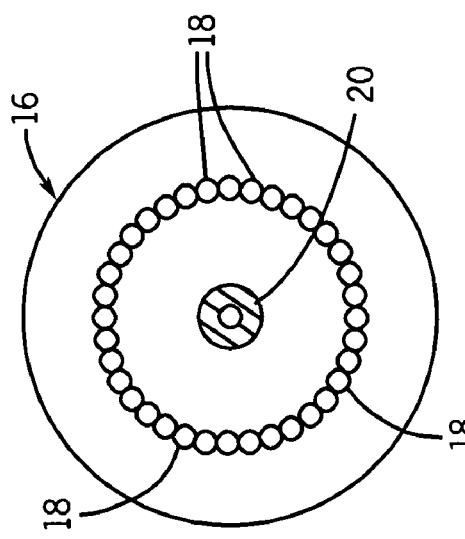
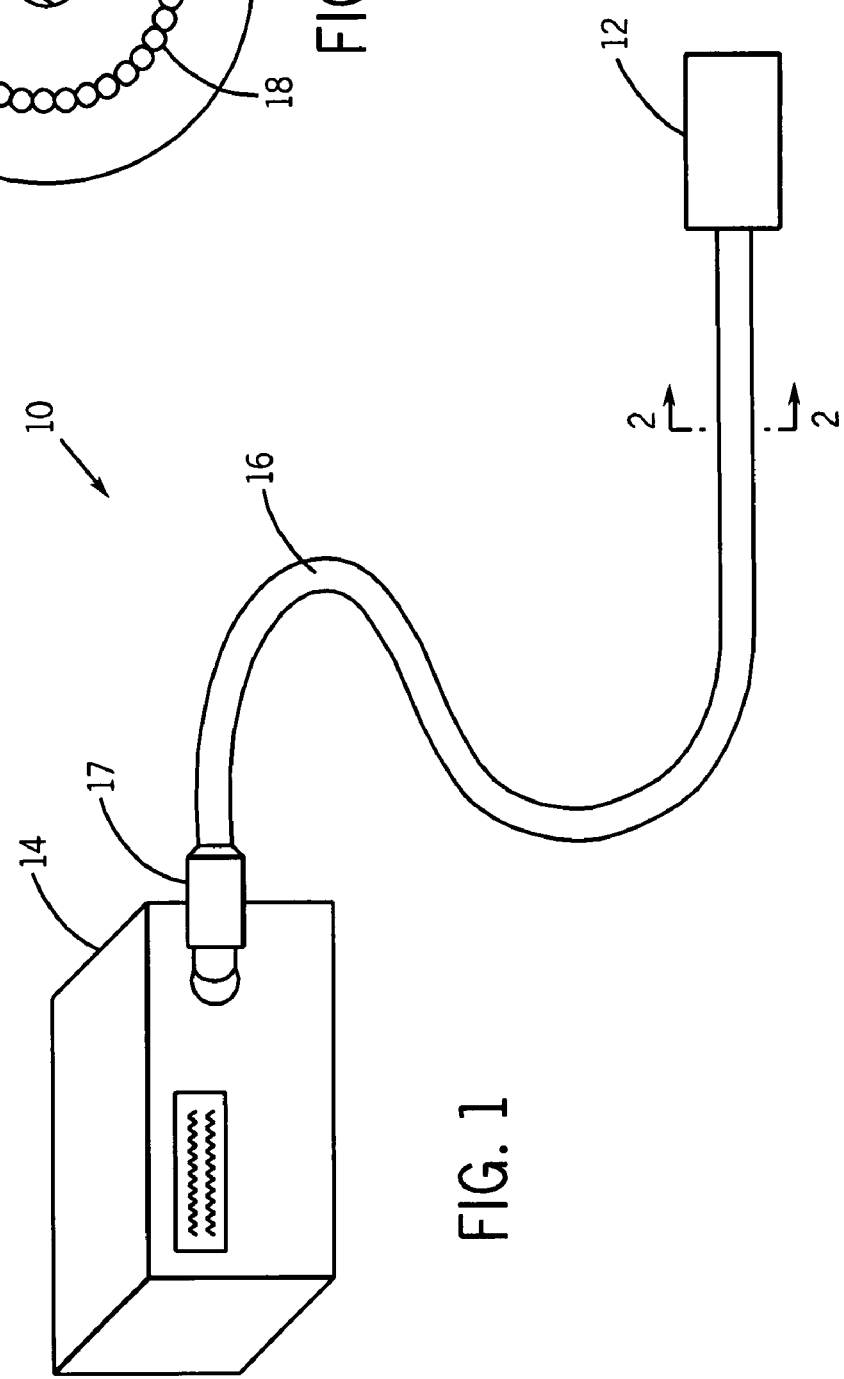
FIG. 2
FIG. 1

METHOD FOR IDENTIFICATION OF SENSOR SITE BY LOCAL SKIN SPECTRUM DATA

BACKGROUND OF THE INVENTION

1. Field of the Invention

The present invention relates generally to medical devices and, more particularly, to the determination of the location of and/or calibration of a medical device.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. For example, to measure certain characteristics, a non-invasive sensor may be utilized that transmits electromagnetic radiation, such as light, through a patient's tissue and then photoelectrically detects the absorption and/or scattering of the transmitted or reflected light in such tissue. The physiological characteristics of interest may then be calculated based upon the amount of light absorbed and/or scattered. In such measurement approaches, the light passed through the tissue is typically selected to be of one or more wavelengths that may be absorbed and/or scattered by one or more constituents of the blood or tissue in an amount correlative to the amount of the constituents present in the blood or tissue. In this manner, the measured amount of light absorbed and/or scattered may then be used to estimate the amount of blood or tissue constituent in the tissue using various algorithms.

One technique for monitoring the physiological characteristics of a patient is commonly referred to as pulse oximetry, and devices built based upon pulse oximetry techniques are commonly referred to as pulse oximeters. Pulse oximetry may be used to measure various blood characteristics, such as the blood-oxygen saturation of hemoglobin in arterial blood, the volume of blood pulsation supplying the tissue, and/or the rate of blood pulsations corresponding to each heart beat of a patient and/or other cardiovascular parameters of interest. Such physiological information allows doctors and other health care personnel to provide the best possible health care for their patients. Similar techniques may be used to measure tissue hydration. These techniques differ from pulse oximetry primarily in the wavelengths selected for use in the sensor, and in the algorithms used to calculate parameters related to tissue hydration.

The monitor used with pulse oximetry sensors and other non-invasive sensors are typically calibrated depending on the type of the sensor to ensure maximum accuracy and specificity. Sensors often contain a calibration element, such as a coded resistor or a memory, to provide calibration information to the monitor. For example, a bandage-style pulse oximetry sensor designed for use on the finger of a patient will provide calibration information for that tissue region and sensor type, while an adhesive-type sensor for use on the forehead of a patient will provide different calibration information.

Unfortunately, technicians or other medical personnel may place a sensor on an inappropriate region, for example by attempting to use a finger sensor on the forehead, resulting in inaccurate measurements of the physiological characteristic of interest, such as blood oxygen saturation. A bandage-style sensor for use on the finger is typically a transmission-type sensor, in which an emitter and detector are placed on opposing sides of the sensor site. The emitter and detector must therefore have a minimum amount of space between them to accommodate the contours of finger. During operation, the emitter shines one or more wavelengths of light through the patient's finger or other tissue, and light received by the detector is processed to determine the blood oxygen saturation or other desired physiological characteristic of the patient.

In contrast, an adhesive-style sensor for use on the forehead, while generally operating by the same technique, is a reflectance-style sensor. Reflectance-style sensors include an emitter and detector that are typically placed on the same side of the sensor. The spacing between the emitter and detector in a reflectance-style sensor is typically much smaller than the spacing between the emitter and detector in a transmission style sensor. The light detected by the detector is light scattered back toward the tissue surface and processed to determine blood oxygen saturation or other physiological characteristic. Thus, if a technician misplaces a transmission-type bandage-style sensor intended for use on a finger on the forehead instead, the spacing between the emitter and detector is not optimized for reflectance-type pulse oximetry. Such misplacement could result in inaccurate measurements of blood oxygen saturation or other physiological characteristics.

Similarly, for tissue hydration assessment, it has been found that the site of sensor placement is important. Particularly, for the purpose of predicting whole body hydration from a local measurement of hydration, knowledge of the site of the sensor placement may critically affect the accuracy of the measurement. For example, placement of the sensor on a body location that is gravitationally above or below the heart, may affect the measurement.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a method for determining the location of a sensor that includes: emitting light into a patient's tissue with at least one emitter disposed on a sensor body; detecting the light with at least one detector disposed on the sensor body; determining a physiological parameter based on the detected light; and determining the location of the sensor based on the parameter.

There is provided a method for operating a sensor that includes: emitting light into a patient's tissue with at least one emitter; detecting the light with at least one detector; determining a patient-specific physiological parameter wherein the patient-specific physiological parameter comprises at least one of skin color, age, gender, pooled blood, venous blood pulsation, or abnormal tissue; and determining calibration information based on the physiological parameter.

A sensor assembly is provided. The sensor assembly includes: a sensor body of a spectrophotometric sensor having an emitter configured to emit light into a patient's tissue and a detector configured to detect the light; and a monitor. The monitor includes an algorithm configured to determine the location of the sensor based on the detected light.

There is also provided another sensor assembly, including: a sensor body of a spectrophotometric sensor having an emitter configured to emit light into a patient's tissue and a detector configured to detect the light; and a monitor. The monitor being configured to determine a physiological parameter from the detected light and configured to select at least one emitter from the plurality of the emitters and at least one detector from the plurality of the detectors based on the physiological parameter.

BRIEF DESCRIPTION OF THE DRAWINGS

Advantages of the invention may become apparent upon reading the following detailed description and upon reference to the drawings in which:

FIG. 1 depicts an exemplary system with a fiber optic sensor for use in accordance with the present techniques;

FIG. 2 depicts a cross-sectional view of the fiber optic sensor cable of FIG. 1 taken along line 2-2 in FIG. 1;

DETAILED DESCRIPTION OF SPECIFIC EMBODIMENTS

Figure 3:
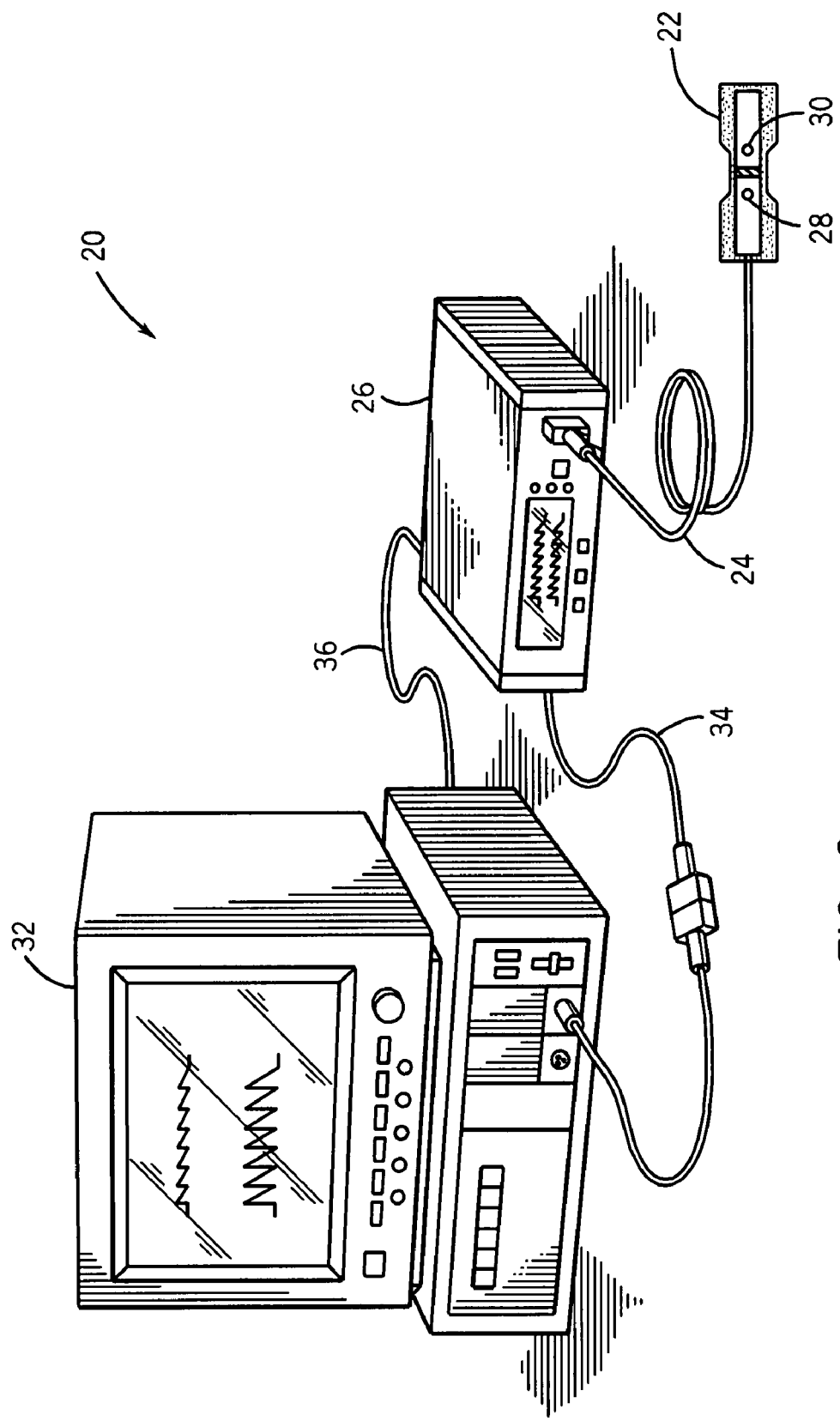
FIG. 3 depicts a pulse-oximetry system with a bandage-style sensor coupled to a patient monitor for use in accordance with the present techniques.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A number of techniques are presently disclosed. For example, it may be desirable to determine the location of a sensor, such as a pulse oximetry sensor or other sensor utilizing spectrophotometry, so that the location of the sensor may be used to calibrate a monitor coupled to the sensor to improve the accuracy of calculations performed by the monitor. The location of the sensor is determined from location-dependent spectra indicating the water content in the epidermis and the dermis, and the relative thickness of those layers. For example, the forehead and finger have a large variation in respective epidermal thickness and are distinguishable by analyzing spectra from each location. Based on a spectral determination of skin thickness as being indicative of the sensor having been placed on a patient's finger or on a patient's forehead, a calibration coefficient specific to a finger or forehead may be chosen among those stored on the sensor and sent to a monitor, or the monitor may choose the calibration coefficient based on location information provided by the sensor.

Further, using a technique described herein, it may also be desirable to determine the skin thickness of a patient at the sensor site without regard to sensor location and to use that determination to calibrate a monitor coupled to the sensor. Instead of selecting a specific sensor location, the monitor may determine skin thickness at the sensor site and select a specific calibration coefficient for that skin thickness. The calibration coefficient may be sent from the sensor to the monitor or it may be selected among those stored on the monitor.

It also may be desirable to determine other physiological parameters, such as skin color, i.e. skin pigmentation, and to calibrate a monitor coupled to the sensor based on this determination. Skin color of a patient at the sensor site may be determined from the absorption of light in a specific spectral region. The monitor may select a calibration coefficient based on a skin color gradient.

Additionally, it may be also desirable to determine the approximate age group of the patient and calibrate a monitor coupled to the sensor based on this determination. Some age groups, e.g. neonates, have a relative higher water content and pooled venous blood than adults. The difference in spectra between a neonate and adult may be used by the monitor to select specific calibration coefficients.

It also may be desirable to identify a patient condition at the sensor site, such as the presence of pooled blood or a tissue edema, and provide a notification to a technician or other medical personnel. Although water content in different layers of the skin is typically responsible for absorption bands in a spectrum of the skin or tissue, other blood or tissue constituents may show absorption bands in various spectral regions. For example, pooled blood at the surface or the skin, or an accumulation of interstitial fluid, e.g. tissue edema, may also show absorption at different spectral regions. A monitor coupled to the sensor may determine the presence of pooled blood or tissue edema and provide the notification.

A multi-site sensor having multiple emitters and/or detectors at various spacings is also provided. Using the techniques described herein, an optimal emitter-detector combination may be chosen by evaluating the spectral information received from the emitters and detectors. Such a sensor may have one emitter-detector spacing suitable for transmission-based operation, and another emitter-detector spacing suitable for reflectance-based operation, for example. Further, such a sensor may provide calibration coefficients to a monitor based on the determination of physiological parameters such as sensor location, skin thickness, etc. For example, the use of more than one source-detector spacing may also aid in determining the thickness of tissue layers, or help resolve the composition of various layers.

The embodiments and techniques described herein rely on spectral analysis for determination of various patient-specific or location-specific physiological parameters or conditions, such as water content, epidermal thickness, skin color, tissue edema, etc. Specifically, for example, embodiments and techniques described herein may implement one of the methods for measuring water in tissue by NIR spectroscopy are described in U.S. Pat. No. 6,591,122; U.S. Pub. No. 2003-0220548; U.S. Pub. No. 2004-0230106; U.S. Pub. No. 2005-0203357; U.S. Ser. No. 11/528,154; U.S. Ser. No. 60/857,045; U.S. Ser. No. 11/283,506; and U.S. Ser. No. 11/282,947 all of which are incorporated herein by reference. Alternatively, an embodiment of the present invention may implement techniques for measuring the analyte concentrations using spectral bandwidth absorption, as described in U.S. Ser. No. 11/528,154, which is also incorporated herein by reference.

For simplicity, the spectral analysis for determination of sensor location based on skin thickness and relative water content will be described below. The technique described below is not limited to water content, as determinations of skin thickness, pooled blood, tissue edema, or other patient or location specific physiological parameters or conditions may be performed in a similar manner. Further, the technique described herein is applicable to any spectrophotometric sensor and may be adapted to any applications requiring such a sensor.

Absorption of various spectral regions reflects the absorption characteristics of different blood and/or tissue constituents and the ability of the light at those spectral regions to penetrate different layers of tissue. Due to the different penetration of light in these spectral regions, the composition and/or thickness of different layers of skin may also be identified from a spectrum of the skin and comparison of relative water absorption bands. For example, light in the spectral region from about 1050 nm to about 1350 nm penetrates into the epidermis and dermis and is therefore useful at determining the composition and/or thickness of the epidermis and dermis. Light in this spectral region will be absorbed by blood and/or tissue constituents that are present in relatively high concentrations in the epidermis and dermis, e.g. water. In contrast, light emitted in the spectral region from about 2000 nm to about 2300 nm is limited to penetration of the stratum corneum layer of the epidermis and is therefore most useful at determining the composition of this layer. However, compared to the lower epidermis and dermis, water content in the stratum corneum is relatively low. Light emitted in the about 1350 to about 1550 nm region has intermediate absorbance between the shorter and longer wavelength regions described above, and is therefore expected to have an intermediate penetration depth. Thus, variations in the intensity ratio between the water absorption band between about 1350 to about 1550 and the water absorption band between about 2000 nm and about 2300 nm can be used to determine the composition and/or thickness of the skin at the measurement site. For example, the stratum corneum is relatively thin at the forehead and cheek, but relatively thick at the finger pad and palm. A spectrum taken at the forehead or cheek will indicate a strong water absorption band in the 1350 to 1550 nm spectral region (relatively high water content in the epidermis and dermis), while a spectrum taken at the finger or palm will indicate a weak water absorption band in the 2000 nm to 2300 nm spectral region (penetration limited to the stratum corneum). Through such an analysis, different spectra may be correlated to specific locations on the body.

In another example, a particularly sensitive method of determining skin thickness may take advantage of the distinctive absorption peaks of lipids. A layer of subcutaneous fat is located just below the dermis, and the relative absorbance by lipids in this layer is indicative of the relative penetration of light into this layer. Distinctive fat absorption bands are located in the vicinity of about 930 nm, about 1210 nm, about 1720 nm, and about 2300 nm wavelengths. For example, for detection of dermal thickness in a patient, a source-detector spacing in the range of about 1 mm to about 5 mm and spectral measurement in the about 1700 nm to about 1800 nm range may be selected.

Further improvement in depth resolution may also be achieved by performing reflectance measurements at more than one source-detector spacing. For example, by comparing absorbance spectra measured at source-detector spacings in the range of about 0.05 mm to about 0.5 mm with spacings in the range of about 1 mm to about 5 mm, the composition of the epidermis and dermis may be respectively determined. Further improvement in the determination of multi-layer tissue composition may be achieved through the combination of both multiple source-detector spacings and multiple spectral regions. For example, a 0.1 mm source-detector separation as described above would be best suited to spectral measurements in the range of about 1800 nm to about 2500 nm, where tissue absorbance is high.

It should be appreciated that exemplary steps of the present technique are typically implemented in a sensor and a patient monitoring system. In accordance with some aspects of the present technique, reusable medical sensors and patient monitors are provided and configured to determine patient-specific physiological parameters.

Fiber Optic Sensor and Calibration of a Monitor Based on Skin Location

Referring now to FIG. 1, a system 10 depicting a fiber optic sensor 12 used in conjunction with a monitor 14 is shown. In the depicted embodiment, a sensor cable 16 connects the sensor 12 to the monitor 14 through a connector 17. The sensor cable 16 is typically used to transmit light, control and/or timing signals from the monitor 14 to the sensor 12 and/or to transmit acquired data from the sensor 12 to the monitor 14. The sensor 12 and/or the sensor cable 16 may include or incorporate one or more integrated circuit devices or electrical devices, such as a memory, processor chip, or resistor that may facilitate or enhance communication between the sensor 12 and the monitor 14.

The sensor cable 16 may contain multiple optic fibers 18 and a central detector fiber 20 as shown in the cross-section of sensor cable 16 taken along line 2-2 as illustrated in FIG. 2. The monitor 14 may contain one or more emitters that emit light through the optic fibers 18. In the exemplary system shown, the emitters used are multiple light emitting diodes (LEDs) or any other kind of emitter that emits light in the desirable wavelengths. Alternatively, the emitter may be a source capable of emitting across a broad range of wavelengths, such as a tunable laser. Each optic fiber 18 may connect to one LED, and a filter may be interposed between each LED and optic fiber 18. Regulation of the desired wavelength of light transmitted to the sensor and into the patient's tissue may be accomplished through the selection of LEDs as well as the filters between the LEDs and the optic fibers 18.

The fiber optic sensor 12 may be placed on a single location on a patient's body and the monitor 14 or the sensor 12 may correlate the spectrum to different locations on the body by analyzing different spectral regions. Specifically, the sensor 12 may be placed on a patient's finger, and a blood oxygen saturation measurement may be taken using the red and infrared spectral regions typical of pulse oximetry. In alternative applications, the sensor 12 may be placed on multiple locations of a patient's body to test for other conditions, such as tissue hydration, for example.

As discussed above, the spectral absorption regions vary according to different blood or tissue constituents and depth of penetration of light in those regions. For example, the relative water absorption bands of different spectral regions may be used to determine epidermal and dermal composition and/or thickness, and therefore sensor location. Accordingly, in addition to the red and infrared spectral regions, the system 10 and fiber optic sensor 12 may be configured to transmit light in the following regions: from about 1050 nm to about 1350 nm; from about 1550 nm to about 1850 nm, and/or from about 2000 nm to about 2300 nm. Variations in the water and fat absorption bands in these spectral regions can be analyzed to determine skin thickness and, therefore, sensor location. A thicker epidermis may indicate a sensor location of a finger, whereas a thinner epidermis may indicate a sensor location of a forehead. Calibration information for the monitor 14, such as calibration coefficients, is selected based on the determination of the sensor location. Calibration coefficients may be stored in a memory on the sensor 12, or they may be stored in the monitor 14 and selected based on information sent from the sensor 12 to the monitor 14. Calibration coefficients may be stored for any number of sensor locations, e.g., the forehead, the finger, the cheek, etc.

Once the monitor is calibrated according to the specific sensor location, the blood oxygen saturation may be determined. The calibration of the monitor 14 for the specific sensor location increases the accuracy and specificity of the monitor's blood oxygen saturation determination.

Fiber Optic Sensor and Calibration of a Monitor Based on Skin Thickness

Accuracy of the system 10 and fiber optic sensor 12 described above may be increased by calibration of the monitor 14 coupled to the sensor 12 according to a determination of skin thickness. In this embodiment, the system 10 and fiber optic sensor 12 operate according to the techniques described above, and may provide additional wavelengths in the following regions: from about 1050 nm to about 1350 nm; from about 1550 nm to about 1850 nm, and from about 2000 nm to about 2300 nm. Methods and algorithms for determining fluid parameters are disclosed in U.S. Pub. No. 2004-0230106, and methods and algorithms for estimating tissue hydration from spectral absorption bandwidth measurements are disclosed in U.S. Ser. No. 11/528,154, both of which have been incorporated herein by reference. Using the relative water absorption bands in these spectral regions, the thickness of the skin may be determined. Instead of correlating the thickness of the skin to a sensor location, however, calibration information may be chosen based on the skin thickness without regard to sensor location. For example, calibration coefficients, either stored in the sensor 12 in a memory or stored in the monitor 14, may be selected along a variable calibration curve, depending on the thickness of the skin, as opposed to discrete locations such as a finger, forehead, etc.

Once the monitor is calibrated according to the specific skin thickness at the sensor site, the blood oxygen saturation may be determined. The calibration of the monitor for the specific skin thickness at the sensor location increases the accuracy and specificity of the monitor's blood oxygen saturation determination.

Fiber Optic Sensor and Calibration of a Monitor Based on Skin Color

Again referring to the exemplary system 10 and fiber optic sensor 12 of FIG. 1, in some embodiments the calibration information used by the monitor may be chosen based on a determination of skin color of the patient at the sensor site, e.g. skin pigmentation. Some wavelengths of light emitted by the optic fibers 18 may be affected by the amount and type of melanin or carotene in the skin. In situations of low blood oxygen saturation, for example, skin color has a relatively larger effect on the accuracy of the blood oxygen saturation determination as compared to patients with normal levels of blood oxygen saturation.

In this embodiment the system 10 and the fiber optic sensor 12 operate according to the techniques described above, and may provide additional wavelengths in the following region: from about 400 nm to about 800 nm. Absorption bands in this spectral region may indicate higher concentrations of melanin (darker skin) or lower concentrations of melanin (lighter skin). Calibration coefficients may be selected based on this determination, and the selection may depend on the on the complexity of the spectral analysis. For example, the selection of calibration coefficients may be based on a threshold, in which melanin concentrations indicative of a skin color darker than the threshold result in selection of one set of calibration coefficients. Conversely, melanin concentrations indicative of a skin color lighter than the threshold result in the selection of a different set of calibration coefficients. In alternate embodiments, instead of a discrete selection based on a threshold value, the calibration coefficients may be selected for ranges of skin color as represented by gradual changes in melanin concentration. Again, calibrating the monitor according to skin color/pigmentation can result in increasing the accuracy and specificity of the monitor's blood oxygen saturation determination, especially in patient's experiencing low levels of blood oxygen saturation.

Fiber Optic Sensor and Calibration of a Monitor Based on Age Group

In other embodiments, the calibration information used by the monitor 14 in the system 10 depicted in FIG. 1 may be chosen based on a determination of the age group of the patient, e.g. whether the patient is a neonate or an adult. In determining the age group of the patient, spectral regions that are indicative of water content and pooled blood are most useful. For example, neonates typically have higher relative water content and pooled blood than adults. A spectrum of the skin of a neonate will show different peak water absorption bands and different peak bands at wavelengths of light susceptible to pooled blood absorption.

As in the above embodiments, the system 10 and fiber optic sensor 12 operate according to the techniques described above, for example by using the red and infrared to determine blood oxygen saturation. The monitor 14 and fiber optic sensor 12 may provide additional wavelengths in the following regions: 510 nm (useful for identifying pooled blood); from about 1050 nm to about 1350 nm; from about 1550 nm to about 1850 nm; and from about 2000 nm to about 2300 nm (useful in identifying water content in different layers of skin). The spectral analysis of these spectral regions may show absorption bands that can be used to determine if the patient is likely to be a neonate or an adult. For example, water absorption bands in the spectral region from about 2000 nm to about 2300 nm may indicate higher relative water content in comparison to a spectrum taken from an adult. Similarly, peak absorption bands around the 510 nm spectral region may indicate pooled blood at the sensor site. Thus, from a combination of these two indicators, the monitor may make a determination that the patient is a neonate and send this information to the monitor. The monitor may store different calibration coefficients specific to neonates or adults and make a selection based on the sensor determination. Alternatively, the sensor 12 can store calibration coefficients in a memory, and the monitor can select a calibration coefficient based on the age group of the patient, and then the sensor can send the appropriate selected calibration coefficient to the monitor 14.

Alternatively, steady-state (as opposed to photoplethysmographic) measurement of the tissue absorbance using standard pulse-oximetry wavelengths such as 660 nm and 890 nm, i.e. red and near infrared wavelengths, may also be useful as an indication of the amount of pooled blood at the measurement site. Advantageously, implementation of such a technique would require no change to the sensor except that calibration for the LED intensity output may be required. Such calibration could be readily accomplished through a separate measurement on a standard scattering material such as Teflon.

Bandage-Style Pulse Oximetry Sensor and Identification of Patient Conditions

Turning now to FIG. 3, a system 20 for use in conjunction with a conventional bandage-style pulse oximetry sensor 22 or the adhesive-style sensor is shown. A monitor 26 is shown connected to an bandage-style sensor 22 through a sensor cable 24. The sensor cable 24 of the sensor 22 may be directly coupled to a pulse oximetry monitor 26, or it may be coupled to a transmission device (not shown) to facilitate wireless transmission between the sensor 22 and the monitor 26. The sensor cable 24 is responsible for transmitting electrical and/or optical signals to and from the emitter 28 and detector 30 of the sensor 22. The monitor 26 may be any suitable pulse oximeter, such as those available from Nellcor Puritan Bennett Inc. Furthermore, to upgrade conventional pulse oximetry provided by the monitor 26 to provide additional functions, the monitor 26 may be coupled to a multi-parameter patient monitor 32 via a cable 34 connected to a sensor input port or via a cable 36 connected to a digital communication port.

Figure 4:
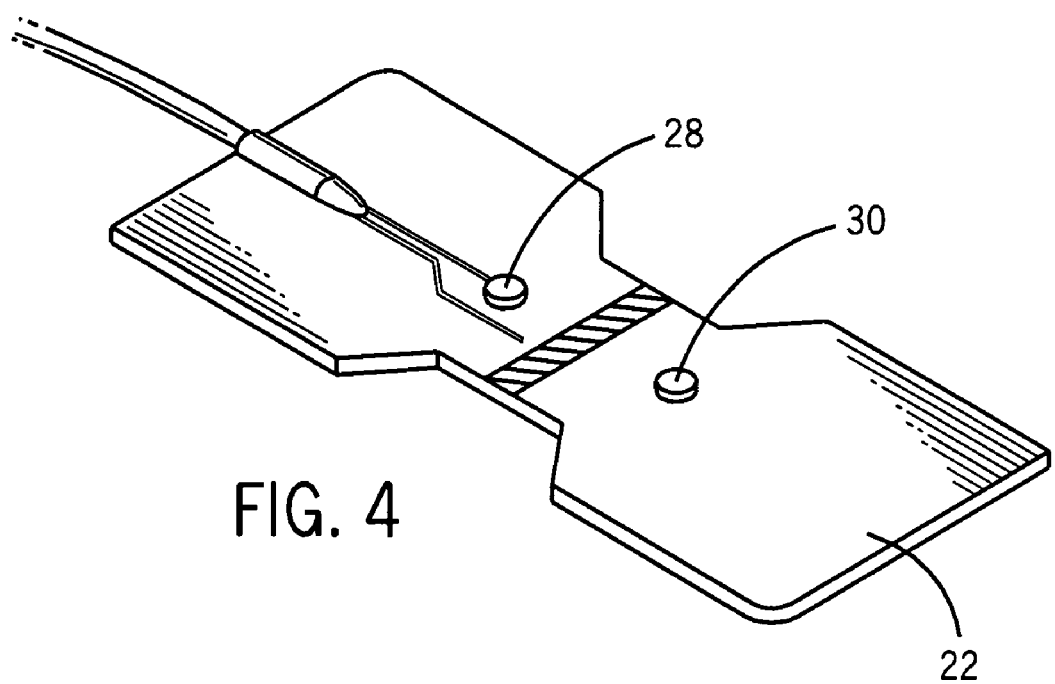
FIG. 4 depicts a close-up of the bandage-style sensor of FIG. 3 for use on a patient's finger, in accordance with the present techniques.

A close-up of the exemplary bandage-style sensor 22 is shown in FIG. 4. The exemplary sensor 22 includes an emitter 28 and a detector 30 which may be of any suitable type. For example, the emitter 28 may be one or more LEDs adapted to transmit one or more wavelengths of light, such as in the visible light or red to infrared range, and the detector 30 may be one or more photodetectors, such as a silicon photodiode package, selected to receive light in the range emitted from the emitter 28. The type and number of detectors 30 present in the sensor 22 may depend on how many and what wavelengths are emitted by the emitter 28. In a conventional pulse-oximetry sensor, the emitter 28 emits light only in the red and infrared range. The exemplary sensor 22 has been modified from a conventional pulse-oximetry sensor so that the emitter 28 may emit one or more wavelengths in addition to those used in pulse oximetry, such as through the addition of another LED.

The additional wavelengths of light emitted by emitter 28 are used to determine one or more patient-specific conditions. For example, a green LED, emitting light at wavelengths about 510 nm, may be added to identify pooled blood underneath the skin. In other embodiments, an LED emitting light at a wavelength of about 980 nm can be used to identify interstitial fluid, and therefore tissue edema, in the underlying tissue. Other LED's may be used depending on the blood or tissue constituent of interest. Regardless of the LED and additional wavelengths chose, operation of the sensor 22 and detection of the transmitted light is similar to conventional pulse oximetry and the spectral analysis described above. The sensor 22 is placed on a patient, for example on a patient's finger, and then light is emitted by the emitter 28, transmitted through the patient's tissue, and then received by the detector 30. The monitor 26 receives signals from the detector 30 and determines blood oxygen saturation from the ratio of the light absorbed emitted at the red and infrared wavelengths. In the exemplary system 20, the monitor 26 also receives signals based on the detected light at the additional wavelengths, for example at about 510 nm for example. The absorption of light at this additional wavelength, such as a peak absorption band around this region, may indicate pooled blood at the sensor site. If the monitor 26 determines there is such a peak absorption band in the spectral region, then the monitor 26 may provide an audio or visual notification. A technician may then take any necessary actions, such as relocating the sensor to a site less affected by the presence of pooled blood. Similar actions may be taken by the monitor 26 if the additional wavelengths emitted provide an indication of tissue edema or other conditions that may affect accuracy of the sensor.

Sensor with Multiple Emitters and Detectors

Figure 5:
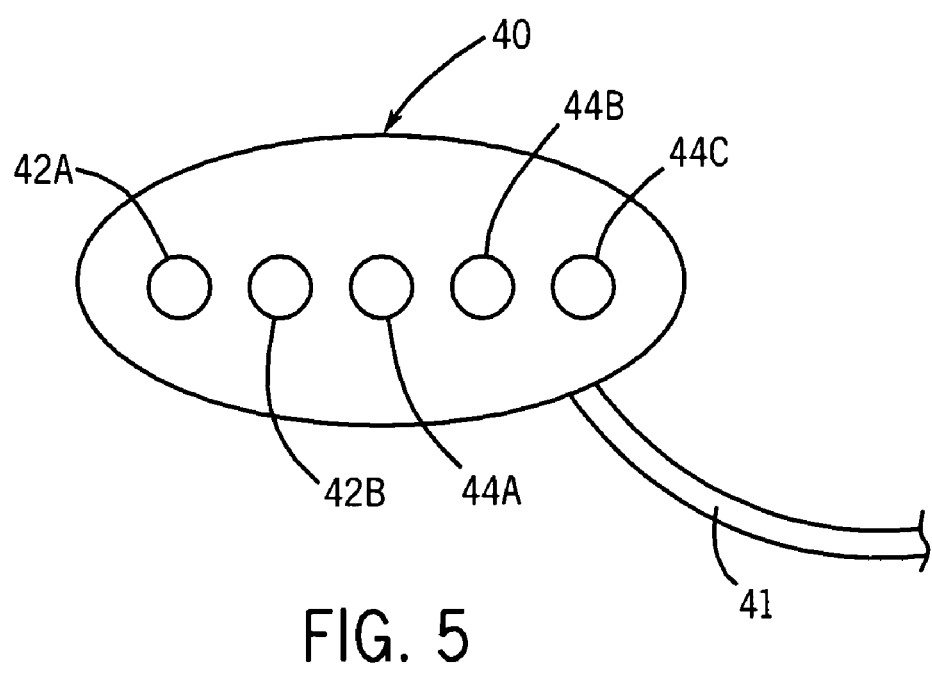
FIG. 5 depicts an adhesive-type medical sensor for use in accordance with the present techniques.

FIG. 5 illustrates an exemplary adhesive-type medical sensor 40 with multiple emitters and detectors for use in pulse oximetry or other spectrophotometric applications. The sensor 40 may be used in the system 20 depicted in FIG. 3 and connected to a monitor 26 by a sensor cable 41. The sensor cable 41 is responsible for transmitting electrical and/or optical signals to and from the emitters 42 and detectors 44 of the sensor 41.

The exemplary sensor 40 has two emitters 42A and 42B and three detectors 44A, 44B, and 44C, but any number of emitters and detectors may be used. The emitters and detectors are spaced inline along the body of the sensor 40, with emitters 42A and 42B grouped together and the three detectors 44A, 44B, and 44C grouped together. In alternate embodiments the spacing between the emitters and detectors and the number of emitters or detectors may vary according to the size of the sensor 40 and the desired spectophotometric application, e.g. reflectance-based or transmission-based operation. The emitters 42A and 42B may be one or more LEDs adapted to transmit one or more wavelengths of light, such as in the red to infrared range, and the detectors 44A, 44B, and 44C may be one or more photodetectors, such as a silicon photodiode package, selected to receive light in the range emitted from the emitters 42A and 42B.

Operation of the sensor 40 may include emission of different wavelengths of light and detection and analysis of the absorption of those wavelengths to determine blood oxygen saturation, water content and skin composition and thickness, and to determine optimal emitter-detector combinations. For example, emitter 42B may emit red and infrared wavelengths for determining blood oxygen saturation. Emitter 42A may emit wavelengths in the spectral regions useful for quantification of water content at different layers of the skin: from about 1050 nm to about 1350 nm; from about 1550 nm to about 1850 nm; and/or from about 2000 nm to about 2300 nm. The detectors 46A, 46B, and 46C may detect any or all of the emitted wavelengths of light as they are transmitted or reflected through the patient's skin or tissue. Further, the sensor may send calibration information to the monitor depending on the determinations of water content, skin thickness, skin composition, etc., as described above.

Additionally, the monitor 26 may select an optimal emitter-detection combination from the emitters 42A and 42B and detectors 44A, 44B, and 44C available on the sensor. The optimal emitter-detector combination may be that combination best arranged for reflectance-based operation or transmission-based operation, depending on the sensor location. Alternatively, the optimal emitter-detector combination may be that combination least susceptible to perturbations, i.e. the presence of venous pulsation or a large artery. It may also be the emitter-detector combination with the appropriate distance for the depth and/or specific optical properties of the tissue of interest, i.e. a closer emitter-detector spacing may be more appropriate for darker skin because of the absorptive characteristics of melanin During operation of the sensor, the monitor may receive signals of varying quality from detectors 44A, 44B, and 44C. For example, if the sensor 40 is applied to the finger as a bandage-style sensor, then emitter 42B and detector 44C are spaced on opposite sides of the finger. This arrangement is optimal for transmission-based operation. In contrast, detector 44A will be near the top of the finger, spaced relatively close to emitters 42A and 42B, in an arrangement suitable for reflectance-based operation. However, the thickness of the skin at the finger may inhibit the effectiveness of reflectance-type operation at that sensor site, and detector 44A may receive minimal reflected light from the emitters 42A and 42B, and therefore may transmit a poor quality signal to the monitor. Alternatively, if the sensor 40 is applied to the forehead, then all emitters and detectors are on the same side of the sensor site. In this application, light received at the detectors 44A, 44B, and 44C will be reflected from the skin, and the emitter-detector pairing that provides the best spacing for reflectance-based operation is optimal. In this case, emitter 42B and detector 44A are spaced in an arrangement best suited for reflectance-type operation, i.e. minimal space between the emitter 42B and detector 44A relative to the other emitter-detector spacings. The optimal source-detector spacing for reflectance may be chosen based on a balance among the following factors: (1) minimizing light shunting, i.e. LED light that reaches the detector without penetrating to the blood layer, by increasing the source-detector spacing; (2) maximizing the size of the plethysmographic signal relative to the steady-state signal by increasing source-detector spacing; (3) maximizing the signal to noise ratio of the plethysmograph signal by using an intermediate source-detector spacing; and (4) minimizing sensitivity to subject-to-subject scattering variations by optimizing at intermediate source-detector spacing.

Once the optimal emitter-detector pairing is selected, the monitor 26 may determine blood oxygen saturation from the absorption of the red and infrared light. Alternative embodiments may provide use of multiple emitter-detector pairings, for example use of the detected light from all three detectors 44A, 44B, and 44C, and determine blood oxygen saturation based on an average or other weighted calculation.

The technique described herein may be used in additional sensor embodiments. For example, a multi-site adhesive-type sensor similar to the sensor described in FIG. 4 may be used, in which the appropriate spectral regions that serve as indicators of epidermal and dermal composition and/or thickness could be used to determine the location of the sensor. The location of the sensor can then be used to select the appropriate calibration information and/or algorithm for that particular location, as outlined in the techniques described above.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to reflectance type sensors, other sensor designs, and measurement of other physiological characteristics such as tissue hydration. Likewise, the present techniques are not limited to any specific location on a patient but may be applied to placement on any body part.

What is claimed is:

1. A method for determining a location of a sensor on a patient's body, comprising:
    emitting light into a patient's tissue with at least one emitter disposed on a sensor body;
    detecting the light with at least one detector disposed on the sensor body;
    determining a physiological parameter based on the detected light;
    determining the location of the sensor based on the parameter; and
    selecting calibration information based on the location of the sensor.

2. The method of claim 1, wherein determining the physiological parameter comprises determining a water content of the patient's tissue.

3. The method of claim 1, wherein determining the physiological parameter comprises determining an epidermal thickness of the patient's tissue.

4. The method of claim 1, wherein determining the physiological parameter comprises determining a dermal thickness of the patient's tissue.

5. The method of claim 1, wherein determining the location of the sensor comprises determining whether the location of the sensor is the forehead of the patient or the finger of the patient.

6. The method of claim 1, wherein the sensor is a pulse oximetry sensor.

7. The method of claim 1, wherein the sensor is a fiber optic sensor.

8. A method of operating a sensor, comprising:
    emitting light into a patient's tissue with at least one emitter;
    detecting the light with at least one detector;
    determining a first patient-specific physiological parameter based on the detected light, wherein the first patient-specific physiological parameter comprises at least one of skin color, age, gender, pooled blood, venous blood pulsation, or abnormal tissue;
    determining a second patient-specific physiological parameter based on the detected light, wherein the second patient-specific physiological parameter is different from the first patient-specific physiological parameter; and
    selecting calibration information for the determination of the second patient-specific physiological parameter based on the first patient-specific physiological parameter.

9. The method of claim 8, wherein determining the second patient-specific physiological parameter comprises determining blood oxygen saturation from the detected light.

10. The method of claim 8, wherein the abnormal tissue comprises tissue edema.

11. The method of claim 8, comprising providing a notification based on the first or the second patient-specific physiological parameter.

12. The method of claim 8, wherein determining the calibration information comprises determining a calibration coefficient based on the first patient-specific physiological parameter.

13. The method of claim 8, comprising selecting one emitter and one detector based on the first patient-specific physiological parameter, wherein the sensor comprises at least two emitters and at least two detectors.

14. The method of claim 13, wherein selecting one emitter and one detector based on the first patient-specific physiological parameter comprises selecting an emitter and a detector with a spacing suitable for operating in transmission mode or reflectance mode.

15. The method of claim 8, wherein the sensor is a pulse oximetry sensor.

16. The method of claim 8, wherein the sensor is a fiber optic sensor.

17. A sensor assembly, comprising:
    a sensor body having an emitter configured to emit light into a patient's tissue and a detector configured to detect the light; and
    a monitor comprising an algorithm configured to determine the location of the sensor on a patient's body based on a physiological parameter from the detected light and an algorithm configured to select calibration information based on the location of the sensor.

18. The assembly of claim 17, wherein the sensor assembly is configured to measure blood oxygen saturation.

19. The assembly of claim 17, wherein the emitter comprises optic fibers.

20. A sensor assembly, comprising:
a sensor body having a plurality of emitters configured to emit light into a patient's tissue and a plurality of detectors configured to detect the light; and
a monitor being configured to determine a location of the sensor body on the patient based on a physiological parameter from the detected light and configured to select at least one emitter from the plurality of the emitters and at least one detector from the plurality of the detectors based on the location of the sensor body.

21. The sensor assembly of claim 20, wherein the physiological parameter comprises skin color.

22. The sensor assembly of claim 20, wherein the monitor is configured to select an emitter and a detector with a spacing suitable for operating in transmission mode or reflectance mode based on the location of the sensor body.

* * * * *